US009445732B2

(12) United States Patent
Lee et al.

(10) Patent No.: US 9,445,732 B2
(45) Date of Patent: Sep. 20, 2016

(54) METHODS AND DEVICE FOR SENSING A PERSON'S PULSE IN TRADITIONAL CHINESE MEDICINE

(71) Applicant: Hong Kong Applied Science and Technology Research Institute Company Limited, Hong Kong (HK)

(72) Inventors: Francis Chee Shuen Lee, Hong Kong (HK); Ho Yin Chan, Hong Kong (HK)

(73) Assignee: Hong Kong Applied Science and Technology Research Institute Company Limited, Shatin, New Territories, Hong Kong (CN)

( * ) Notice: Subject to any disclaimer, the term of this patent is extended or adjusted under 35 U.S.C. 154(b) by 799 days.

(21) Appl. No.: 13/872,135

(22) Filed: Apr. 28, 2013

(65) Prior Publication Data

US 2014/0323886 A1    Oct. 30, 2014

(51) Int. Cl.
*A61B 5/02*     (2006.01)
*A61B 5/0255*   (2006.01)
*A61B 5/00*     (2006.01)

(52) U.S. Cl.
CPC ............ *A61B 5/0255* (2013.01); *A61B 5/4854* (2013.01)

(58) Field of Classification Search
None
See application file for complete search history.

(56) References Cited

U.S. PATENT DOCUMENTS

| 4,980,626 A | * | 12/1990 | Hess | ...................... B25J 9/1005 |
| | | | | 250/559.33 |
| 8,052,185 B2 | | 11/2011 | Madhani | |
| 2005/0218679 A1 | * | 10/2005 | Yokoyama | ............... B25J 15/10 |
| | | | | 294/99.1 |
| 2006/0145494 A1 | * | 7/2006 | Nihei | ..................... B25J 9/1612 |
| | | | | 294/106 |
| 2007/0260356 A1 | * | 11/2007 | Kock | ..................... B25J 9/1641 |
| | | | | 700/261 |
| 2010/0259057 A1 | * | 10/2010 | Madhani | ............. B25J 15/0009 |
| | | | | 294/106 |

FOREIGN PATENT DOCUMENTS

| CN | 201279134 Y | 7/2009 |
| CN | 101049247 B | 5/2010 |

(Continued)

OTHER PUBLICATIONS

Duc et al. Designing 8 Degrees of Freedom Humanoid Robotic Arm. International Conference on Intelligent and Advanced Systems (2007).*

(Continued)

*Primary Examiner* — Etsub Berhanu
(74) *Attorney, Agent, or Firm* — Ella Cheong Hong Kong; Sam T. Yip

(57) ABSTRACT

This invention discloses a pulse-sensing device and methods for pulse sensing. In one embodiment, the device includes a robotic finger comprising a humanoid-finger structure, and an actuating-force transferring member for transferring an actuating force to the structure at an actuation point thereon and along an actuation direction. One end of the structure is pivotally mounted to a fulcrum and another end has a sensing area. The robotic finger is configured such that, when the sensing area contacts a person's wrist, a first perpendicular distance from the fulcrum to a first line is substantially longer than a second perpendicular distance from the fulcrum to a second line, where the first line is a straight line passing through a sensing point of the sensing area and being substantially perpendicular to the sensing area, and the second line is a straight line passing through the actuation point and orienting along the actuation direction.

14 Claims, 4 Drawing Sheets

(56) References Cited

FOREIGN PATENT DOCUMENTS

| | | |
|---|---|---|
| CN | 101732039 A | 6/2010 |
| CN | 102579018 A | 7/2012 |
| TW | 200727865 A1 | 8/2007 |
| TW | 200816958 A | 4/2008 |
| TW | I327061 B | 7/2010 |
| TW | 201132333 A1 | 10/2011 |

OTHER PUBLICATIONS

Luo et al. Stringlike Pulse Quantification Study by Pulse Wave in 3D Pulse Mapping. The Journal of Alternative and Complementary Medicine, vol. 18, No. 10, 2012, pp. 924-931.*

Office Action issued from the State Intellectual Property Office of the People's Republic of China on Jun. 26, 2014, including a search report.

* cited by examiner

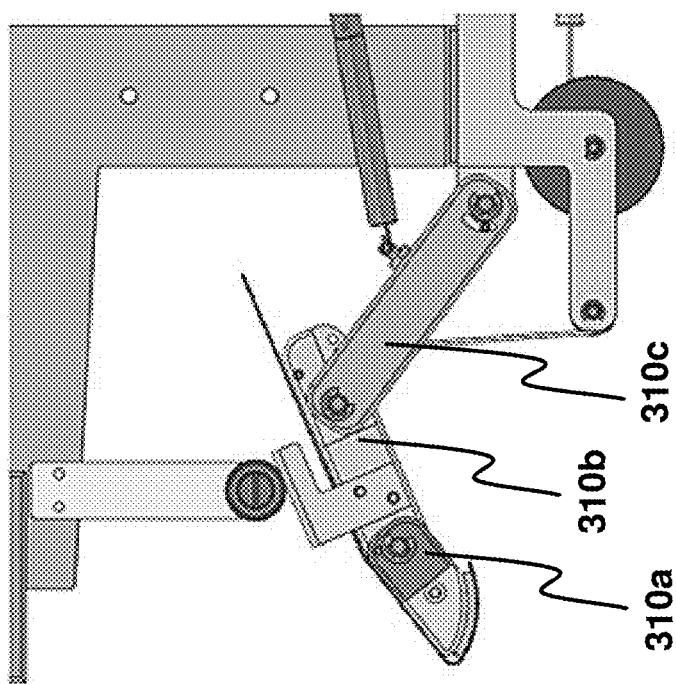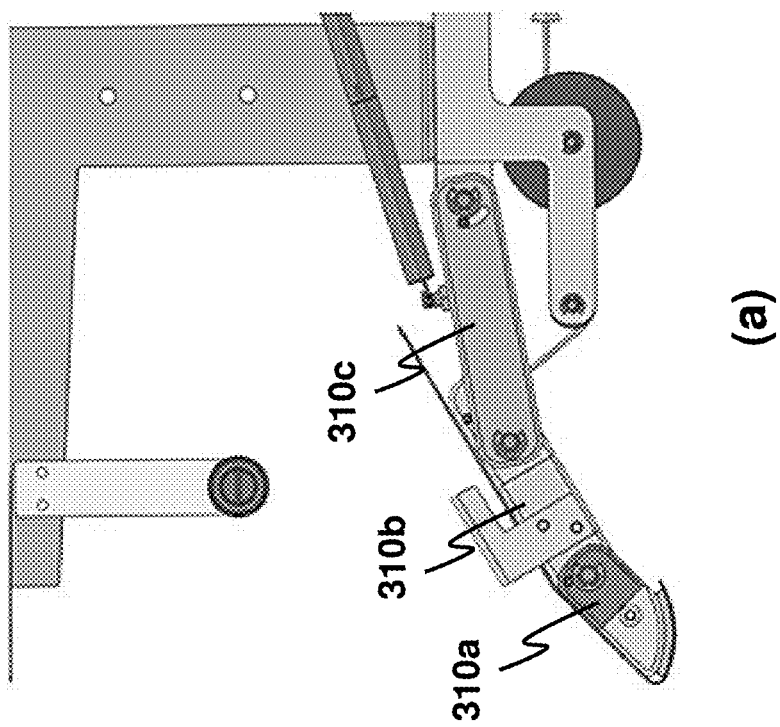
FIG. 4

ND DEVICE FOR SENSING A
METHODS AND DEVICE FOR SENSING A PERSON'S PULSE IN TRADITIONAL CHINESE MEDICINE

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates generally to machine-based sensing of a person's pulse in the practice of traditional Chinese medicine. In particular, the present invention relates to such machine-based sensing by a mechanical configuration having at least an advantage of diminishing a disturbance in an actuating force during the sensing of the person's pulse.

BACKGROUND

In traditional Chinese medicine (TCM), a Chinese medicine practitioner (CMP) performs pulse palpation by manually sensing, at three levels: a superficial level, a middle level and a deep level, a person's pulse at a number of different locations on the radial artery around the wrist of the person. By sensing and analyzing the signal of the pulse, the CMP performs medical diagnosis on the person, i.e. the patient, according to medical principles of the TCM.

In recent years, it is possible to perform pulse sensing by a device. Machine-based sensing of a person's pulse provides certain advantages over pulse sensing by CMPs. These advantages include efficiency and repeatability. In addition, a signal processor can be used to process the signal sensed by the pulse-sensing device, thereby enabling implementation of an automatic medical-diagnosis system.

In a pulse-sensing device, an actuator is usually used to move and position a pulse-sensing sensor onto a person's wrist. Typically, as in disclosures of CN101049247, TW20113233 and TW200727865, the actuator is of a linear-translation type so that an actuating force is directly applied to the sensor for making a linear movement. When the sensor is pressed onto the wrist, a certain level of the actuating force is still maintained in order to secure the sensor onto the wrist for pulse sensing. In general, the actuator generates the actuating force that is subject to random noisy fluctuation. This noisy fluctuation is directly superimposed onto the sensor, which is usually a pressure sensor for pulse sensing, so that the sensed signal of the person's pulse is significantly corrupted by the noisy fluctuation of the actuating force. Although one can considerably reduce this noisy fluctuation by using a hydraulic actuator (which can be configured to achieve a high degree of stability in the generated actuating force), the hydraulic actuator is bulky, difficult for maintenance, and expensive. Advantageously, it is desirable to have a light-weight, low-cost pulse-sensing device.

There is a need in the art for a pulse-sensing device that a sensed signal of the pulse is not significantly impacted by a noisy disturbance of an actuating force without a need to employ a highly-stable actuator.

SUMMARY OF THE INVENTION

In a first aspect of the present invention, a pulse-sensing device having at least an advantage of diminishing a resultant disturbance resulted from a disturbance in an actuating force during sensing a person's pulse is provided.

The pulse-sensing device comprises one or more humanoid fingers, at least one of which is a robotic finger. The robotic finger comprises a humanoid-finger structure having a finger-tip end and a posterior end. The posterior end is pivotally mounted to a fulcrum on the pulse-sensing device so that the structure is rotatable about the fulcrum. The finger-tip end has a sensing area configured for sensing a signal of a person's pulse when the person's wrist is in contact to the sensing area. The robotic finger further comprises an actuating-force transferring member for transferring an actuating force to the humanoid-finger structure such that the actuating force is applied to an actuation point located on the structure, and is directed to the structure along an actuation direction. In particular, the robotic finger is configured such that, when the person's wrist is in contact to the sensing area for sensing the signal of the person's pulse, a first perpendicular distance from the fulcrum to a first line is substantially longer than a second perpendicular distance from the fulcrum to a second line, where the first line is a straight line passing through a sensing point of the sensing area and being substantially perpendicular to the sensing area, and the second line is a straight line passing through the actuation point and orienting along the actuation direction.

The humanoid-finger structure comprises a first sensor on the sensing area for acquiring and measuring the signal of the person's pulse. The first sensor may be a pulse-sensing sensor array for detecting the signal of the person's pulse at a plurality of locations over the sensing area, where the pulse-sensing sensor array has pre-determined curvature for mimicking a human finger tip, and is configured to provide a hardness level close to human-skin stiffness. The pulse-sensing sensor array may be of a capacitive type.

Preferably, the robotic finger further comprises a second sensor for measuring a resultant force experienced at the actuation point. When the person's wrist is in contact to the sensing area, a reaction force generated by the person's wrist mechanical property and the blood pressure pulse at the sensing area is amplified by the humanoid-finger structure and then captured by the second sensor.

The robotic finger may be configured such that a pressing force produced by the humanoid-finger structure on the person's wrist when the person's wrist is in contact to the sensing area is controllable. A desired value of the pressing force for application to the person's wrist is determined according to a pulse-sensing stage selected from Fu, Zhong and Chen in the doctrines of TCM. In addition, a pneumatic actuator may be used in the pulse-sensing device for generating the actuating force to be received by the actuating-force transferring member, and the pressing force is controllable to achieve the desired value by directing the pneumatic actuator to produce the actuating force according to a continuous pressure regulating principle.

It is preferable that the humanoid-finger structure comprises multiple sections sequentially arranged and end-to-end pivotally-jointed, configuring the humanoid-finger structure to be foldable.

Additionally, the robotic finger may further comprise a restoring element for exerting about the fulcrum a retreating torque that opposes an advancing torque resulted from the actuating force. It allows the actuation direction of the actuating force to remain unidirectional when switching the humanoid-finger structure from an engaged position of making the sensing area contact the person's wrist to a disengaged position of detaching the sensing area away from the person's wrist, and vice versa. The restoring element may be a spring having one end fixed to the humanoid-finger structure.

The pulse-sensing device may use a pneumatic actuator for generating the actuating force to be received by the actuating-force transferring member. The device may further include an optical locating device for locating the person's wrist so as to guide the humanoid-finger structure to accurately position the sensing area on the person's wrist.

The finger-tip end may include a finger tip on which the sensing area is located, wherein the finger tip is detachable. Optionally, the one or more humanoid fingers are individually controllable. An inter-finger distance between any adjacent two of the one or more humanoid fingers may be adjustable.

In the pulse-sensing device, it is preferable that each of the one or more humanoid fingers is configured as the robotic finger.

A second aspect of the present invention is to provide a first method for sensing a signal of a person's pulse by a humanoid-finger structure. The humanoid-finger structure has a finger-tip end and a posterior end, the posterior end being pivotally mounted to a fulcrum, the finger-tip end having a sensing area configured to sense the signal.

The first method comprises applying an actuating force, directed along an actuation direction, to the humanoid-finger structure at an actuation point located on the structure in order to position the humanoid-finger structure such that the sensing area is in contact to the person's wrist. The actuation point and the actuation direction are selected such that, when the person's wrist is in contact to the sensing area for sensing the signal of the person's pulse, a first perpendicular distance from the fulcrum to a first line is substantially longer than a second perpendicular distance from the fulcrum to a second line, where: the second line is a straight line passing through the actuation point and orienting along the actuation direction; and the first line is a straight line passing through a sensing point of the sensing area and being substantially perpendicular to the sensing area. It follows that an undesired disturbance caused by a disturbance in the actuating force to the signal sensed at the sensing area is substantially diminished, and that a signal experienced at the actuation point is amplified.

Preferably, the first method further comprises acquiring and measuring the signal of the person's pulse by a first sensor on the sensing area, and measuring a resultant force experienced at the actuation point by a second sensor so that a reaction force generated by the person's wrist mechanical property and the blood pressure pulse at the sensing area is amplified by the humanoid-finger structure and then captured by the second sensor.

The first method may further include sensing the signal of the person's pulse by combining a first set of measurement data obtained from the first sensor and a second set of measurement data obtained from the second sensor. Alternatively, after the signal is sensed, the signal may be analyzed according to the first and the second sets of measurement data.

In a third aspect of the present invention, a second method for sensing a signal of a person's pulse is provided.

The second method comprises sensing the signal by a mechanical structure having a sensing area, a first sensor on the sensing area for acquiring and measuring the signal when the person's wrist is in contact to the sensing area, and a second sensor for measuring a resultant force experienced at an actuation point of the mechanical structure. In the second method, an actuating force is applied at the actuation point for positioning the sensing area to contact the person's wrist. Furthermore, the mechanical structure is configured by a mechanical configuration such that the following two desired results are obtained. First, a disturbance in the actuating force is scaled down by a first factor at the sensing area so as to cause a diminished, undesired disturbance to the signal acquired and measured by the first sensor, where the first factor is greater than unity and is determinable by the mechanical configuration. Second, a reaction force generated by the person's pulse at the sensing area is scaled up by a second factor substantially similar to the first factor when producing the resultant force experienced at the actuation point.

BRIEF DESCRIPTION OF THE DRAWINGS

FIG. 4 depicts, in accordance with an embodiment of the present invention, the robotic finger in: (a) an engaged position configured for positioning the robotic finger to contact a person's wrist; and (b) a disengaged position.

DETAILED DESCRIPTION OF THE INVENTION

A first aspect of the present invention is to provide a pulse-sensing device having at least an advantage of diminishing a resultant disturbance caused by a disturbance in an actuating force to a signal of the person's pulse.

In the practice of TCM, a CMP puts his or her fingers on a person's wrist to sense the person's pulse. In an analogous way, a pulse-sensing device may be configured with a number of "mechanical fingers" for pulse sensing. Advantageously, each of the mechanical fingers may employ a humanoid-finger structure in order to mimic the CMP's finger in pulse sensing.

Figure 1:
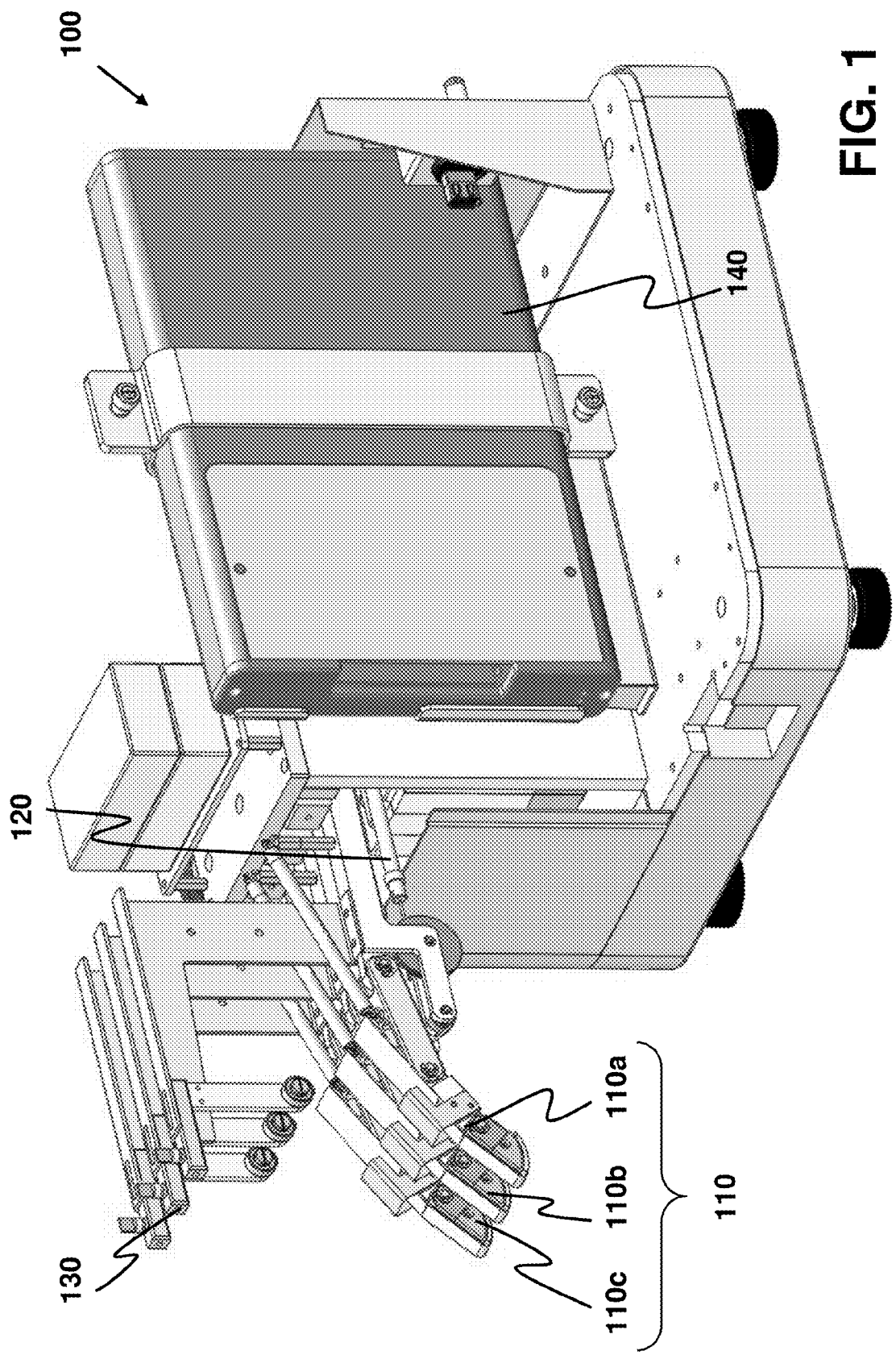
FIG. 1 is a pulse-sensing device in accordance with an embodiment of the present invention.
Figure 2:
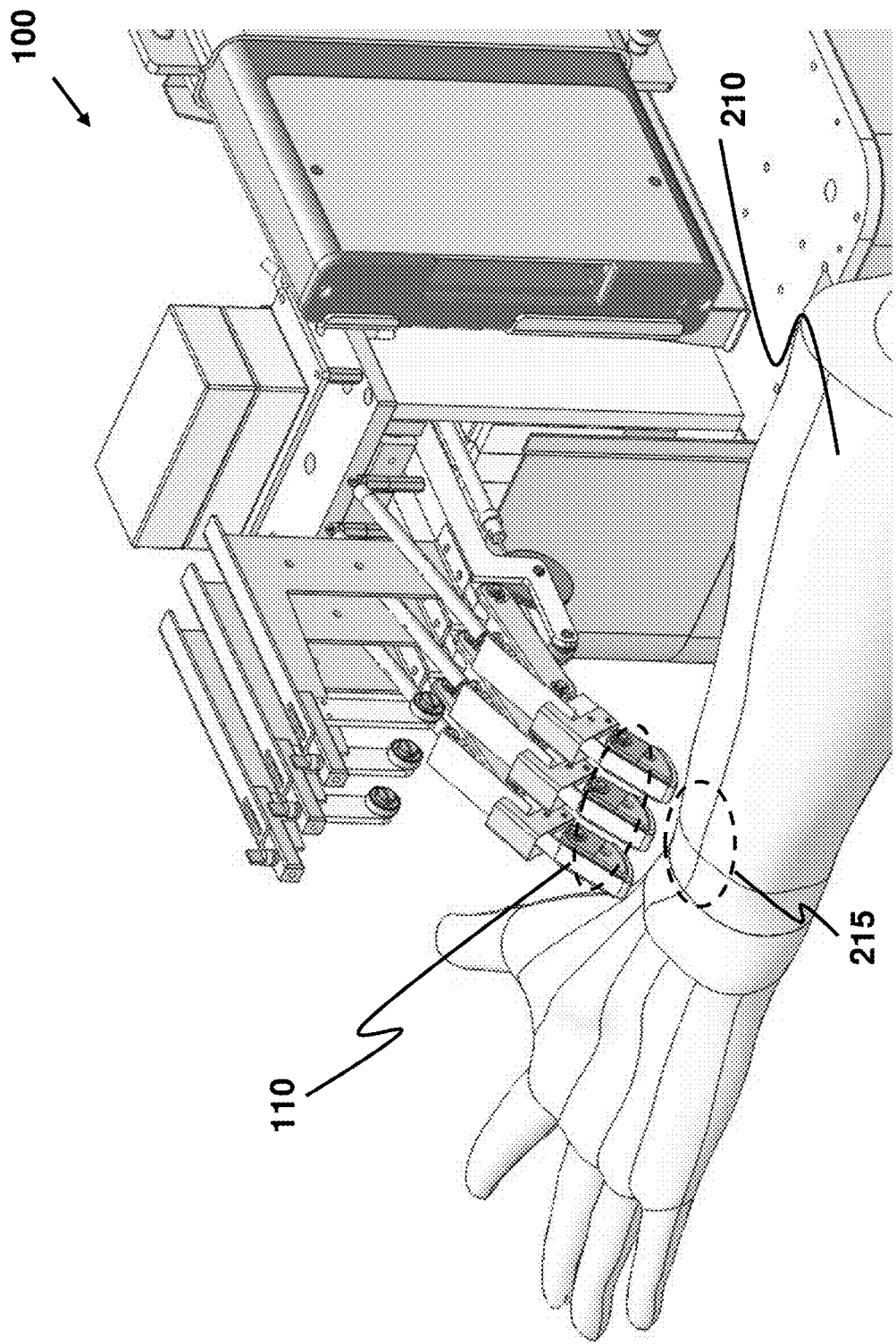
FIG. 2 illustrates how the pulse-sensing device performs pulse sensing on a person's wrist.

A pulse-sensing device as disclosed herein in the present invention comprises one or more humanoid fingers. FIG. 1 depicts a pulse-sensing device according to an embodiment of the present invention. A pulse-sensing device 100 comprises one or more humanoid fingers 110 each of which is configured to be positioned on a location of a person's wrist for sensing the person's pulse. As illustrated in an example use of the pulse-sensing device 100 shown in FIG. 2, the one or more humanoid fingers 110 are positioned above and pressed onto an area 215 of an upper limb 210 of a person, where the area 215 is around a wrist of the person, such that the person's pulse can be sensed by the one or more humanoid fingers 110. In accordance with the practice of TCM, a CMP usually uses three fingers for pulse sensing. Accordingly, it is preferable to employ three humanoid fingers 110a, 110b and 110c in the pulse-sensing device 100. To position the one or more humanoid fingers 110 onto the wrist, an actuator 120, which may be a single actuator or may be composed of a plurality of constituting actuators, is used for providing an actuating force to move each of the humanoid fingers 110. To achieve light-weight low-cost realization of the pulse-sensing device 100, the actuator 120 is preferred to be a pneumatic actuator. In addition, the pulse-sensing device 100 may include an optical locating element 130 so that accurate positioning of the one or more humanoid fingers 110 onto the wrist is achievable. The pulse-sensing device 100 may further include a data acquisition and processing unit 140 to analyze a pulse signal, single- or multi-dimensional, acquired and sensed by the one or more humanoid fingers 110.

Figure 3:
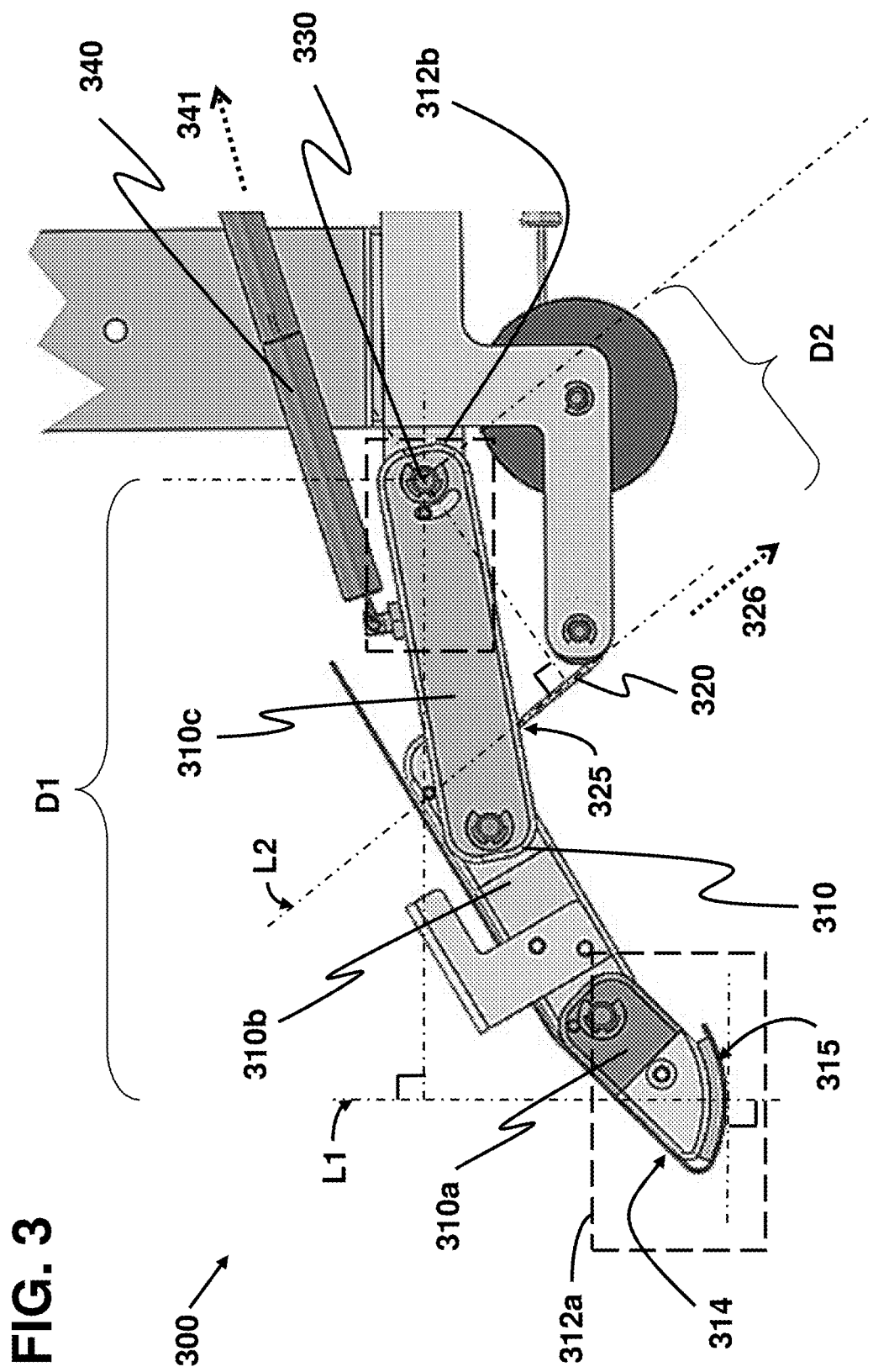
FIG. 3 depicts a robotic finger of the pulse-sensing device in accordance with an exemplary embodiment of the present invention.

According to the present invention, the pulse-sensing device 100 advantageously uses a mechanical configuration for realizing the humanoid fingers 110 in order to substantially diminish an undesired disturbance caused by a noisy disturbance in the actuating force to a pulse signal, where the pulse signal is sensed by the one or more humanoid fingers 110. FIG. 3 depicts a robotic finger 300 having the aforementioned mechanical configuration in accordance with an exemplary embodiment of the present invention. In the pulse-sensing device 100, at least one of the one or more humanoid fingers 110 is realized as the robotic finger 300. Preferably, each of the one or more humanoid fingers 110 is configured as the robotic finger 300.

The robotic finger 300 comprises a humanoid-finger structure 310 having a finger-tip end 312a and a posterior end 312b. The finger-tip end 312a has a sensing area 315 configured for sensing a signal of a person's pulse when the person's wrist is in contact to the sensing area 315. The posterior end 312b is pivotally mounted to a fulcrum 330 so that the structure 310 is rotatable about the fulcrum 330. Note that the fulcrum 330 is located on a part of the pulse-sensing device 100 other than the humanoid-finger structure 310. The robotic finger 300 further comprises an actuating-force transferring member 320 for transferring an actuating force to the humanoid-finger structure 310 such that the actuating force is applied to an actuation point 325 located on the structure 310, and is directed to the structure 310 along an actuation direction 326. The actuating-force transferring member 320 may be implemented as a part of a mechanical assembly, where the mechanical assembly receives the actuating force from the actuator 120 and then transfers the actuating force to the humanoid-finger structure 310 at the actuation point 325 along the actuation direction 326.

Let D1 be a first perpendicular distance from the fulcrum 330 to a first line L1 where the first line L1 is a straight line passing through a sensing point of the sensing area 315 and being substantially perpendicular to the sensing area 315. The sensing point, as used herein, is a representative contact point on the sensing area 315 when the person's wrist contacts the sensing area 315. Since the sensing area 315 may not be flat due to, for example, curvature introduced for mimicking a CMP's finger tip, the first line L1 being substantially perpendicular to the sensing area 315 is defined as that the first line L1 is substantially perpendicular to a surface tangential to the sensing point. Let D2 be a second perpendicular distance from the fulcrum 330 to a second line L2 where the second line L2 is a straight line passing through the actuation point 325 and orienting along the actuation direction 326. The robotic finger 300 is configured such that D1 is substantially longer than D2 when the person's wrist is in contact to the sensing area 315 for sensing the signal of the person's pulse. This mechanical configuration enables an undesired disturbance caused by a disturbance in the actuating force to the signal sensed at the sensing area 315 to be substantially diminished due to the following observation. Denote $\Delta Fa$ as the disturbance in the actuating force and $\Delta Fs$ as the resultant undesired disturbance to the signal sensed at the sensing area 315. As the net moment about the fulcrum 330 is zero in a static condition, it follows that $\Delta Fa \times D2 = \Delta Fs \times D1$. Since the mechanical configuration requires that the ratio D2/D1 is substantially less than unity, it follows that $\Delta Fs/\Delta Fa$ is also substantially less than unity, so that the resultant undesired disturbance caused by the disturbance in the actuating force is substantially diminished. Note that the resultant undesired disturbance is diminished by a factor of D1/D2.

In the robotic finger 300, the humanoid-finger structure 310 comprises a first sensor on the sensing area 315 for acquiring and measuring the signal of the person's pulse. Advantageously, the first sensor may be a pulse-sensing sensor array for detecting the signal of the person's pulse at a plurality of locations over the sensing area 315 where the pulse-sensing sensing sensor array has pre-determined curvature for mimicking a human finger tip and is configured to provide a hardness level close to human-skin stiffness in order to, for instance, reproduce a feeling of touching by a human finger tip to the person's wrist. A configuration that enables provision of such hardness level is to put a layer of soft material underneath the sensor array, where the soft material layer has a hardness level close to human-skin stiffness. An example of a material useful to realize this layer is silicon elastomer. The pulse-sensing sensor array may be implemented as a piezoelectric array, a piezoresistive array, or a capacitive array. The capacitive array is preferable over the other two arrays due to a relatively higher sensitivity.

Preferably, the robotic finger 300 further comprises a second sensor for measuring a resultant force experienced at the actuation point 325. The second sensor can be advantageously used in that a reaction force generated by the person's wrist mechanical property and the blood pressure pulse at the sensing area 315 is amplified at the actuation point 325 by the humanoid-finger structure 310, as demonstrated as follows. Denote $\Delta Fsp$ as the reaction force generated by the person's wrist mechanical property and the blood pressure pulse at the sensing area 315 and $\Delta Fap$ as the corresponding force produced at the actuation point 325. Under a static condition, the net moment about the fulcrum 330 is zero, so that $\Delta Fsp \times D1 = \Delta Fap \times D2$. Since D1/D2 is substantially greater than unity, it follows that $\Delta Fap/\Delta Fsp$ is also substantially greater than unity. Hence, the reaction force generated by the person's wrist mechanical property and the blood pressure pulse at the sensing area 315 is amplified at the actuation point 325. The amplified signal is then captured by the second sensor. Note that the amplification ratio is D1/D2.

It is noteworthy that there is a reciprocal relationship between the factor of diminishing the resultant undesired disturbance caused by the disturbance in the actuating force and the factor of amplifying the reaction force generated by the person's wrist mechanical property and the blood pressure pulse. The disturbance in the actuating force is scaled down by a first factor at the sensing area 315, where the first factor is greater than unity. The aforesaid reaction force is scaled up by a second factor substantially similar to the first factor when producing a resultant force experienced at the actuation point 325.

Advantageously, the robotic finger may be configured such that a pressing force produced by the humanoid-finger structure 310 on the person's wrist when the person's wrist is in contact to the sensing area is controllable. A desired value of the pressing force for application to the person's wrist may be determined according to a pulse-sensing stage selected from Fu, Zhong and Chen in the doctrines of TCM. If a pneumatic actuator is used as the actuator 120 for generating the actuating force to be received by the actuating-force transferring member 320, the pressing force may be made controllable to achieve the desired value by directing the pneumatic actuator to produce the actuating force according to a continuous pressure regulating principle.

Preferably, the humanoid-finger structure 310 is an assembly comprising multiple sections sequentially arranged and end-to-end pivotally-jointed, such that the humanoid-finger structure 310 is configured to be foldable. The multiple sections are labeled as references 310a, 310b and 310c in FIG. 3 for illustration; nevertheless, the number of the multiple sections is not limited only to 3 in the present invention. FIG. 4 illustrates two configurations of the humanoid-finger structure 310 if it is foldable: (a) an engaged position where the sensing area 315 contacts the person's wrist and (b) a disengaged position where the humanoid-finger structure 310 is not deployed. In the engaged position, the humanoid-finger structure 310 is configured to be substantially fully extended. In the disengaged position, the humanoid-finger structure 310 is folded up.

It is preferable that the robotic finger 300 further comprises a restoring element 340 for exerting, about the fulcrum 330, a retreating torque (turning in a direction 341) that opposes an advancing torque resulted from the actuating force (turning in the actuation direction 326). In the presence of the restoring element 340, the actuation direction 326 of the actuating force is allowed to remain unidirectional when switching the humanoid-finger structure 310 from the engaged position to the disengaged position, and vice versa. Keeping the actuation direction 326 unidirectional without switching over from one direction to another is advantageous in that implementation of the actuator 120 and the actuating-force transferring member 320 can be made simple. The restoring element 340 may be a spring having one end fixed to the humanoid-finger structure 310 and another end attached to elsewhere so as to obtain the retreating torque turning in the direction 341.

In one embodiment, the finger-tip end 312a of the humanoid-finger structure 310 includes a finger tip 314 on which the sensing area 315 is located. Optionally, the finger tip 314 is detachable for advantages such as convenience in sensor maintenance and flexibility to provide different finger-tip curvatures and degrees of imitated human-skin stiffness for different patients.

It is also optional that the one or more humanoid fingers 110 may be individually controllable. Individual control of multiple humanoid fingers 110 allows the pressing forces exerted by these multiple humanoid fingers 110 to be individually customizable according to the advanced practice in TCM such that more informative sensing of the person's pulse may result.

Advantageously, an inter-finger distance may be adjustable. The inter-finger distance is a distance between any adjacent two of the one or more humanoid fingers 110. Since people may be different in age, body size, etc., having the inter-finger distance adjustable enables the one or more humanoid fingers 110 to be optimally positioned for pulse sensing according to individualized consideration for different people.

A second aspect of the present invention is to provide a first method for sensing a signal of a person's pulse by a humanoid-finger structure. The humanoid-finger structure has a finger-tip end and a posterior end. The posterior end is pivotally mounted to a fulcrum. The finger-tip end has a sensing area configured to sense the signal. The first method that is disclosed herein is directly derivable from the disclosure above regarding the first aspect of the present invention.

In an exemplary embodiment of the first method, an actuating force, directed along an actuation direction, is applied to the humanoid-finger structure such that the sensing area is in contact to the person's wrist. The actuation point and the actuation direction are selected such that when the person's wrist is in contact to the sensing area for sensing the signal of the person's pulse, a first perpendicular distance from the fulcrum to a first line is substantially longer than a second perpendicular distance from the fulcrum to a second line. The first line is a straight line passing through a sensing point of the sensing area and being substantially perpendicular to the sensing area. The second line is a straight line passing through the actuation point and orienting along the actuation direction. As is mentioned above, an undesired disturbance caused by a disturbance in the actuating force to the signal sensed at the sensing area is substantially diminished.

Preferably, the first method further includes acquiring and measuring the signal of the person's pulse by a first sensor on the sensing area, and measuring a resultant force experienced at the actuation point by a second sensor so that a reaction force generated by the person's pulse at the sensing area is amplified by the humanoid-finger structure and then captured by the second sensor. It yields a first set of measurement data obtained from the first sensor, and a second set of measurement data obtained from the second sensor. In one approach, sensing the signal of the person's pulse may be accomplished by combining the first and the second sets of measurement data. In another approach, the signal is analyzed according to the first and the second sets of measurement data.

A third aspect of the present invention is to provide a second method for sensing a signal of a person's pulse. This second method is directly derivable from the disclosure above regarding the first aspect of the present invention.

In an exemplary embodiment of the second method, the signal is sensed by a mechanical structure. The mechanical structure has a sensing area, a first sensor on the sensing area for acquiring and measuring the signal when the person's wrist is in contact to the sensing area, and a second sensor for measuring a resultant force experienced at an actuation point of the mechanical structure. An actuating force is applied at the actuation point for positioning the sensing area to contact the person's wrist. According to the exemplary embodiment of the second method, the mechanical structure is configured by a mechanical configuration such that (a) a disturbance in the actuating force is scaled down by a first factor at the sensing area so as to cause a diminished, undesired disturbance to the signal acquired and measured by the first sensor, the first factor being greater than unity and determinable by the mechanical configuration, and (b) a reaction force generated by the person's pulse at the sensing area is scaled up by a second factor substantially similar to the first factor when producing the resultant force experienced at the actuation point.

Similar to the first method, a first set of measurement data is obtained from the first sensor and a second set of measurement data is obtained from the second sensor. In one approach, sensing the signal of the person's pulse may be accomplished by combining the first and the second sets of measurement data. In another approach, the signal is analyzed according to the first and the second sets of measurement data.

The present invention may be embodied in other specific forms without departing from the spirit or essential characteristics thereof. The present embodiment is therefore to be considered in all respects as illustrative and not restrictive.

The scope of the invention is indicated by the appended claims rather than by the foregoing description, and all changes that come within the meaning and range of equivalency of the claims are therefore intended to be embraced therein.

What is claimed is:

1. A pulse-sensing device comprising one or more humanoid fingers, at least one of which is a robotic finger comprising:
  a humanoid-finger structure having a finger-tip end and a posterior end, the posterior end being pivotally mounted to a fulcrum on the pulse-sensing device so that the structure is rotatable about the fulcrum, the finger-tip end having a sensing area configured for sensing a signal of a person's pulse when the person's wrist is in contact to the sensing area, the humanoid-finger structure further comprising a first sensor on the sensing area for acquiring and measuring the signal of the person's pulse; and
  an actuating-force transferring member for transferring an actuating force to the humanoid-finger structure such that the actuating force is applied to an actuation point located on the structure, and is directed to the structure along an actuation direction;
  wherein:
  the robotic finger is configured such that, when the person's wrist is in contact to the sensing area for sensing the signal of the person's pulse, a first perpendicular distance from the fulcrum to a first line is substantially longer than a second perpendicular distance from the fulcrum to a second line, where the second line is a straight line passing through the actuation point and orienting along the actuation direction and the first line is a straight line passing through a sensing point of the sensing area and being substantially perpendicular to the sensing area, in order to substantially diminish an undesired disturbance caused by a disturbance in the actuating force to the signal sensed at the sensing area, and to amplify a signal experienced at the actuation point; and
  the robotic finger further comprises a second sensor for measuring a resultant force experienced at the actuation point so that, when the person's wrist is in contact to the sensing area, a reaction force generated by the person's wrist and blood pressure pulse at the sensing area is amplified by the humanoid-finger structure and then captured by the second sensor.

2. The device of claim 1, wherein the first sensor is a pulse-sensing sensor array for detecting the signal of the person's pulse at a plurality of locations over the sensing area, and wherein the pulse-sensing sensor array has pre-determined curvature for mimicking a human finger tip and is configured to provide a hardness level close to human-skin stiffness.

3. The device of claim 1, wherein the robotic finger is configured such that a pressing force produced by the humanoid-finger structure on the person's wrist when the person's wrist is in contact to the sensing area is controllable.

4. The device of claim 3, further comprising a pneumatic actuator for generating the actuating force to be received by the actuating-force transferring member, wherein the pressing force is controllable to achieve a pre-determined value by directing the pneumatic actuator to produce the actuating force according to a continuous pressure regulating principle.

5. The device of claim 1, wherein the humanoid-finger structure comprises multiple sections sequentially arranged and end-to-end pivotally-jointed, configuring the humanoid-finger structure to be foldable.

6. The device of claim 1, wherein the robotic finger further comprises a restoring element for exerting, about the fulcrum, a retreating torque that opposes an advancing torque resulted from the actuating force, allowing the actuation direction of the actuating force to remain unidirectional when switching the humanoid-finger structure from an engaged position of making the sensing area contact the person's wrist to a disengaged position of detaching the sensing area away from the person's wrist, and vice versa.

7. The device of claim 6, wherein the restoring element is a spring having one end fixed to the humanoid-finger structure.

8. The device of claim 7, further comprising a pneumatic actuator for generating the actuating force to be received by the actuating-force transferring member.

9. The device of claim 8, further comprising an optical locating device for locating the person's wrist so as to guide the humanoid-finger structure to accurately position the sensing area on the person's wrist.

10. The device of claim 1, wherein the finger-tip end includes a finger tip on which the sensing area is located, and wherein the finger tip is detachable.

11. The device of claim 1, wherein the one or more humanoid fingers are individually controllable.

12. The device of claim 1, wherein an inter-finger distance between any adjacent two of the one or more humanoid fingers is adjustable.

13. A method for sensing a signal of a person's pulse by a humanoid-finger structure, the humanoid-finger structure having a finger-tip end and a posterior end, the posterior end being pivotally mounted to a fulcrum, the finger-tip end having a sensing area configured to sense the signal, the method comprising:
  applying an actuating force, directed along an actuation direction, to the humanoid-finger structure at an actuation point located on the structure in order to position the humanoid-finger structure such that the sensing area is in contact to the person's wrist, wherein the actuation point and the actuation direction are selected such that, when the person's wrist is in contact to the sensing area for sensing the signal of the person's pulse, a first perpendicular distance from the fulcrum to a first line is substantially longer than a second perpendicular distance from the fulcrum to a second line, where the second line is a straight line passing through the actuation point and orienting along the actuation direction and the first line is a straight line passing through a sensing point of the sensing area and being substantially perpendicular to the sensing area, in order to substantially diminish an undesired disturbance caused by a disturbance in the actuating force to the signal sensed at the sensing area, and to amplify a signal experienced at the actuation point;
  acquiring and measuring the signal of the person's pulse by a first sensor on the sensing area; and
  measuring a resultant force experienced at the actuation point by a second sensor so that a reaction force generated by the person's pulse at the sensing area is amplified by the humanoid-finger structure and then captured by the second sensor.

14. A method for analyzing a signal of a person's pulse, comprising:
   sensing the signal according to the method of claim 13; and
   analyzing the signal according to a first set of measurement data obtained from the first sensor and a second set of measurement data obtained from the second sensor.

* * * * *